US011839479B2

(12) United States Patent
Smith et al.

(10) Patent No.: US 11,839,479 B2
(45) Date of Patent: Dec. 12, 2023

(54) TRUE ONSET IDENTIFICATION

(71) Applicant: Preventice Technologies, Inc., Rochester, MN (US)

(72) Inventors: Richard M. Smith, Oronoco, MN (US); James Dean Hutchins, Advance, NC (US); John Henry Engel, Rochester, MN (US); Michael McRoberts, Mazeppa, MN (US)

(73) Assignee: BOSTON SCIENTIFIC CARDIAC DIAGNOSTIC TECHNOLOGIES, INC., Rochester, MN (US)

( * ) Notice: Subject to any disclaimer, the term of this patent is extended or adjusted under 35 U.S.C. 154(b) by 25 days.

(21) Appl. No.: 16/687,156

(22) Filed: Nov. 18, 2019

(65) Prior Publication Data
US 2020/0155025 A1    May 21, 2020

Related U.S. Application Data

(60) Provisional application No. 62/769,370, filed on Nov. 19, 2018.

(51) Int. Cl.
| A61B 5/316 | (2021.01) |
| A61B 5/00 | (2006.01) |
| G16H 40/67 | (2018.01) |
| G16H 50/20 | (2018.01) |
| A61B 5/361 | (2021.01) |

(52) U.S. Cl.
CPC ............ *A61B 5/316* (2021.01); *A61B 5/0006* (2013.01); *A61B 5/361* (2021.01); *G16H 40/67* (2018.01); *G16H 50/20* (2018.01)

(58) Field of Classification Search
CPC ....... A61B 5/316; A61B 5/361; A61B 5/0006; A61B 5/0205; A61B 5/7264; G16H 40/67; G16H 50/20; G16H 80/00
See application file for complete search history.

(56) References Cited

U.S. PATENT DOCUMENTS

2016/0022164 A1* 1/2016 Brockway .............. A61B 5/726
                                                        600/509
2018/0206752 A1* 7/2018 Bardy ...................... A61B 5/35

OTHER PUBLICATIONS

Wen et al, Real-time ECG telemonitoring system design with mobile phone platform, Measurement, vol. 41, Issue 4, 2008, pp. 463-470, ISSN 0263-2241, https://doi.org/10.1016/j.measurement.2006.12.006. (Year: 2008).*

* cited by examiner

*Primary Examiner* — Ankit D Tejani
*Assistant Examiner* — Ranjani Mari Sundaresan
(74) *Attorney, Agent, or Firm* — Faegre Drinker Biddle & Reath LLP

(57) ABSTRACT

Techniques for identifying onset of a cardiac event. Embodiments receive biometric data measured by at least one remote monitoring device, the biometric data comprising an electrocardiogram (ECG) data relating to a patient. It is determined that the ECG data includes a plurality of critical rhythms, and one of the plurality of critical rhythms is identified as an onset event. The ECG data is modified, based on the identified onset event. The modified ECG data facilitates treatment of the patient related to the identified onset event.

15 Claims, 8 Drawing Sheets

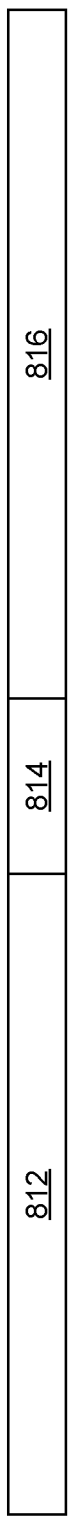
FIG. 8

TRUE ONSET IDENTIFICATION

CROSS-REFERENCE TO RELATED APPLICATIONS

This application claims benefit to U.S. provisional application Ser. No. 62/769,370 filed on Nov. 19, 2018. The aforementioned related patent application is herein incorporated by reference in its entirety.

BACKGROUND

Portable monitoring devices for collecting biometric data are becoming increasingly common in diagnosing and treating medical conditions in patients. For example, mobile devices can be used to monitor cardiac data in a patient. This cardiac monitoring can empower physicians with valuable information regarding the occurrence and regularity of a variety of heart conditions and irregularities in patients. Cardiac monitoring can be used, for example, to identify abnormal cardiac rhythms, so that critical alerts can be provided to patients, physicians, or other care providers and patients can be treated.

BRIEF DESCRIPTION OF THE DRAWINGS

So that the manner in which the features of the present disclosure can be understood in detail, a more particular description of the disclosure, briefly summarized above, may be had by reference to embodiments, some of which are illustrated in the appended drawings. It is to be noted, however, that the appended drawings illustrate only exemplary embodiments and are therefore not to be considered limiting of its scope, may admit to other equally effective embodiments.

FIG. 8 further illustrates bridging events from an ECG data strip, according to one embodiment.

To facilitate understanding, identical reference numerals have been used, where possible, to designate identical elements that are common to the figures. It is contemplated that elements and features of one embodiment may be beneficially incorporated in other embodiments without further recitation.

DESCRIPTION OF EXAMPLE EMBODIMENTS

Overview

Figure 1:
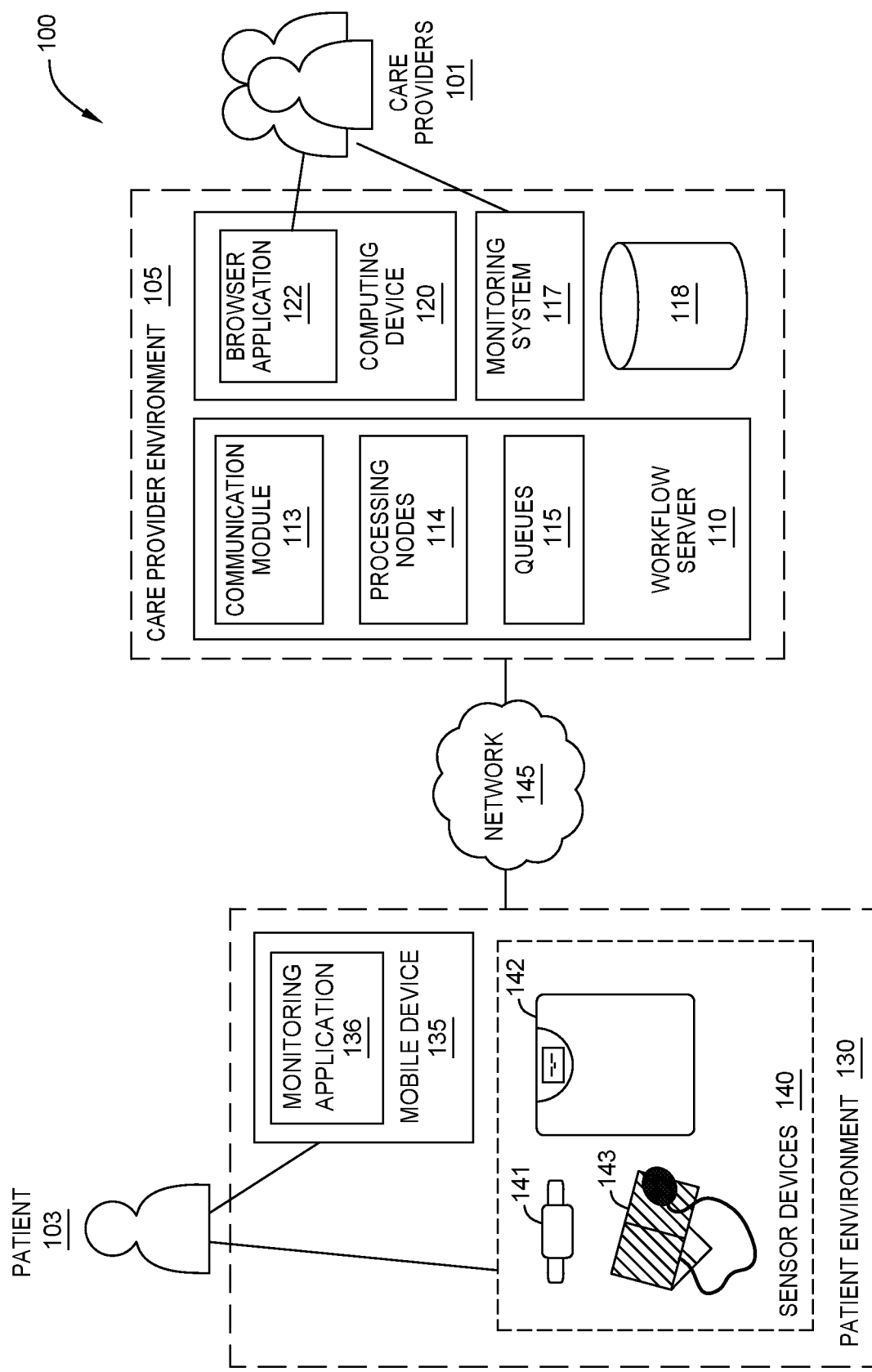
FIG. 1 illustrates an example computing environment, according to one embodiment.

An embodiment described herein is a method for identifying onset of a cardiac event. The method includes receiving biometric data measured by at least one remote monitoring device, the biometric data including an electrocardiogram (ECG) data relating to a patient. The method further includes determining, using a computer processor, that the ECG data includes a plurality of critical rhythms, and identifying one of the plurality of critical rhythms as an onset event. The method further includes modifying the ECG data, using the computer processor, based on the identified onset event. The modified ECG data facilitates treatment of the patient related to the identified onset event.

Another embodiment is a non-transitory computer-readable medium containing computer program code that, when executed on a computer processor, performs an operation for identifying onset of a cardiac event. The operation includes receiving biometric data measured by at least one remote monitoring device, the biometric data including an electrocardiogram (ECG) data relating to a patient. The operation further includes determining that the ECG data includes a plurality of critical rhythms, and identifying one of the plurality of critical rhythms as an onset event. The operation further includes modifying the ECG data based on the identified onset event. The modified ECG data facilitates treatment of the patient related to the identified onset event.

Another embodiment is a system for identifying onset of a cardiac event. The system includes a processor and a memory storing a program, which, when executed on the processor, performs an operation. The operation includes receiving biometric data measured by at least one remote monitoring device, the biometric data including an electrocardiogram (ECG) data relating to a patient. The operation further includes determining that the ECG data includes a plurality of critical rhythms, and identifying one of the plurality of critical rhythms as an onset event. The operation further includes modifying the ECG data based on the identified onset event. The modified ECG data facilitates treatment of the patient related to the identified onset event.

EXAMPLE EMBODIMENTS

As part of mobile cardiac monitoring, a remote monitoring device can collect electrocardiogram (ECG) data for a patient, and transmit the ECG data to a remote server or device for classification and processing. This ECG data can be transmitted in strips, representing ECG readings for a particular period of time (e.g., a few seconds, a few minutes, or longer). A remote server or device can evaluate the strip of ECG data to identify abnormal cardiac rhythms, or other issues, and generate events.

In some circumstances, multiple abnormal cardiac rhythms or other issues can be seen in a given strip ECG of data for a patient, or across multiple ECG data strips for the patient. These abnormal cardiac rhythms (or other issues) can signify cardiac events for a patient. A remote server or device evaluating the ECG data can identify the cardiac events, and can take an action upon identifying an event (e.g., providing treatment to a patient, providing notification to a care provider, or providing an alert to a monitoring service).

To facilitate treatment of patients, it is desirable to identify the true onset of a cardiac event. That is, given identification of a cardiac event based on ECG data, it is desirable to identify the point at which the onset of the cardiac event occurred and any precipitating event. This true onset information can then be provided to a patient, care provider, or monitoring service, and used in treatment of the patient. Further, the true onset can be used itself to facilitate treatment of the patient.

Identifying the true onset of a cardiac event has many advantages. For example, often only a small portion of a patient's ECG data is viewed by a patient care provider, representing a small window in time. Identifying the true onset allows a patient care provider to view ECG data surrounding the onset of the event (e.g., a minute on either side of the onset) to provide more accurate diagnosis and treatment. Further, because only a small slice of ECG data is provided to a care provider, in some circumstances the ECG data does not even include the onset of the relevant cardiac event. Identifying the true onset allows the system to ensure that ECG data relating to the onset is provided to the care provider for diagnosis and treatment.

Further, identifying the true onset can have multiple technical advantages in the care provider environment. In some circumstances, as discussed further below with regard to FIG. 1, a remote monitoring device (e.g., a sensor device 140) can provide ECG data to a mobile device (e.g., a mobile device 135), which can upload the ECG data to a server (e.g., workflow server 110) in a care provider environment (e.g., care provider environment 105). The server, or mobile device, can be responsible for classifying the ECG data to identify cardiac events. But failure to identify the true onset of an event can lead to unnecessary reclassification and wasted processing by the server or mobile device.

For example, a mobile device (or sensor device) may initially classify a cardiac event based on a portion of ECG data, and the server may re-classify the data. Doing so allows for a more computationally expensive analysis of the biometric data to be performed using the computing resources of the server, rather than the limited resources of the sensor devices or the mobile device, while quickly determining an initial classification for the event using the sensor devices or mobile device. Alternatively, or in addition, the sensor device may initially classify a cardiac event and the mobile device may re-classify the event.

In either case, the initial classification can be inaccurate if the mobile device (or sensor device) does not evaluate the true onset. The re-classifying device (e.g., the server or mobile device) may be forced to re-classify data that is incorrectly classified by the mobile device or sensor device, because the mobile device or sensor device evaluated a portion of the ECG data that did not include the true onset. By identifying the true onset, re-classification by the server or mobile device can be limited, speeding up processing, eliminating wasted computer processing resources, saving power and battery life, etc.

In an embodiment, the initial classification can be done through matching patterns of biometric data. For example, the sensor device (or mobile device) could be preprogrammed to recognize one or more patterns of biometric data indicative of an occurrence of the health-related event, and upon detecting a portion of the collected biometric data matches one of the preprogrammed patterns, the device could detect that the event has occurred and could classify the event with an initial classification based on the matching pattern. For example, the device could be configured with various patterns of biometric data, each corresponding to either a cardiac event or a diabetic event. Upon determining that a portion of the collected biometric data matches a pattern corresponding to a cardiac event, the device could initially classify the portion of biometric data as an occurrence of a cardiac event. Another device (e.g., a server or mobile device) can then re-classify the event.

As an example, the sensor device could initially classify the event as a cardiac event, based on monitored ECG data collected from the patient matching a predetermined pattern indicative of a cardiac event. A server could then process the collected ECG data to determine which specific sub-classification of cardiac event occurred. As such processing can be significantly more computationally intensive than the initial pattern matching, the server may be better suited for performing the complex analysis (e.g., utilizing a data center or cloud computing environment's vast resources) than the sensor device or even the mobile device.

Further, one or more of the techniques described herein can allow for lower sensitivity in a cardiac monitoring device. By using these techniques, onset events can be accurately identified using data collected with a lower sensitivity monitoring device. As another example, data transmission and bandwidth use can be reduced. Unnecessary strips of ECG data (e.g., strips too short to identify the onset of an event) need not be transmitted to the server or mobile device, saving transmission bandwidth and overhead.

In an embodiment, one or more of the true onset techniques described herein (e.g., as described in relation to FIG. 4) are performed following classification of an event for a patient. This has many potential advantages. As one example, these techniques can be used to accurately determine the time at which an event onset. For example, a classified event can have a meta-data property signifying when the event occurred (e.g., RecordDate). Once the true onset of the event is identified, the associated property can be changed to reflect the time at which the onset of the event actually occurred.

As another example, a classified event may be the result of an earlier-occurring (and perhaps more significant) event. The true onset techniques can identify this earlier event as the true onset of the patient's condition, and can adjust the classification of the event accordingly (e.g., recording the earlier event and modifying the meta-data associated with the strip). This results in fewer event classifications, meaning less data transmission, recording, and analysis. The classified events are also more accurate. This allows for more accurate prioritization (e.g., as discussed below with regard to FIG. 3), and is more useful for physicians and other care providers. As another example, identifying the true onset can result in fewer false negatives by identifying events that might have otherwise been missed.

FIG. 1 illustrates an example computing environment 100, according to one embodiment. As shown, the computing environment 100 may include a care provider environment 105 and a patient environment 130, each connected to one another via a network 145. The care provider environment 105 and the patient environment 130 allow a care provider 101 (e.g., a technician, nurse, physician, etc.) to monitor biometric data generated by the patient 103.

The care provider environment 105 includes a workflow server 110, a computing device 120, monitoring system 117 and data repository 118. Each of the workflow server 110, the computing device 120, and the monitoring system 117 may be a physical computing system or a virtual computer instance (e.g., executing in a cloud computing platform). A care provider 101 may use the computing device 120 to access (e.g., via a browser application 122, a native application on device 120, etc.) a user interface (UI) hosted by the monitoring system 117.

Of note, although shown as a single entity, the data repository 118 can represent multiple, separate data stores (e.g., relational databases). Moreover, these data stores can span multiple computing nodes. To this end, the separate data stores could be made to function as a single data store (e.g., through data replication techniques and through the use of load balancers). As such, the data repository 118 is representative of any sort of data store on any number of computing systems, consistent with the functionality described herein.

Additionally, although not shown, the data repository 118 may store data from and/or service requests from various other entities, such as third party applications, partners and affiliates, electronic medical record systems, external monitoring devices and products, analytics engines, data consolidator applications and so on. More generally, it is contemplated that the data repository 118 and, more generally, other elements within the care provider environment 105, can interact with any number of different data originators and receipts, consistent with the functionality described herein. As such, the computing environment 100 is provided merely for illustrative purposes only and without limitation.

The workflow server 110 includes applications and data executed to identify and handle health events corresponding to the patient 103. As shown, workflow server 110 includes a communication module 113, processing nodes 114, and queues 115. In one embodiment, the processing nodes 114 are software code or applications that perform a predetermined task or action on received data (e.g., health events). The workflow server 110 evaluates data received from the patient environment 130 using a set of interconnected processing nodes 114 and the queues 115 which form a workflow. As the biometric data or health events are received from the patient environment 130, the workflow may classify (or reclassify) the data to identify a type of the health event—e.g., presentation or notification to patient/care provider, suppression, classification, aggregation, computation, prioritization/triage, and the like. For example, different types of data received from the patient environment 130 may trigger different types of health events—e.g., an irregular heartbeat may trigger a cardiac event, while a signal indicated an electrode has become detached triggers a maintenance event. In one embodiment, at least one sensor device 140 within the patient environment 130 or a monitoring application 136 installed as part of a mobile device 135 within the patient environment 130 may have performed an initial classification of the data or health events. Nonetheless, the workflow server 110 may evaluate the biometric data (or maintenance data) to confirm that this initial classification was correct or to re-classify the event (e.g., as discussed above).

Each type of health event may take a different path through the workflow. That is, different health events may traverse the processing nodes 114 and the queues 115 using different paths. For example, a cardiac event may be evaluated using different processing nodes 114 in the server 110 than a maintenance event. Furthermore, paths through the workflow for the same health event may differ based on a variety of factors such as the severity of the health event, age of the patient 103, other symptoms exhibited by the patient 103, medication taken by the patient 103, and the like. For example, a high priority cardiac event may skip one or more of the processing nodes 114 or the queues 115 and be immediately displayed to the care provider 101 using the monitoring system 117.

The communication module 113 permits the workflow server 110 to receive the data from the patient environment 130 and transmit data to the care providers 101. The communication module 113 may receive data from the at least one sensor device 140 which is used to identify a health event and a corresponding path through interconnected ones of the processing nodes 114 and the queues 115. The communication module 113 helps the care providers 101 complete the workflow by use of the monitoring system 117 and the computing device 120. Moreover, in addition to receiving the data from the patient environment 130, the communication module 113 may enable the workflow server 110 to transmit requests or instructions to the patient environment 130 such as asking the patient 103 if she has any symptoms or instructing the patient 103 to reattach a disconnected electrode (not shown) of the at least one sensor device 140.

In one embodiment, a path used by a health event to traverse the workflow server 110 may include processing nodes 114 that process the health event without user intervention as well as the processing nodes 114 that require input from the care providers 101. For example, one of the processing nodes 114 may filter or screen a health event to determine what queue to place the event, compare the event to one or more rules to determine an action to perform, or store the event. Alternatively, others of the processing nodes 114 may require the care provider 101 to perform an action or provide instructions. For example, the monitoring system 117 may generate a user interface (UI) for a health event which is then displayed to the care provider 101 by the browser application 122. Once the care provider 101 performs an action (e.g., confirms the classification of the event or agrees with an action suggested by the workflow server 110), the remaining operations of the workflow are performed—e.g., send a notification to the patient 103, log the event in the history of the patient 103, route the event to a different one of the care providers 101, reclassify the health event (if the care provider 101 indicated the initial classification was incorrect), or prioritize or triage the health event.

With continued reference to FIG. 1, the patient environment 130 includes the mobile device 135 and the at least one sensor device 140. The mobile device 135 includes the monitoring application 136 which permits communication between the at least one sensor device 140 and the care provider environment 105 via the network 145. The monitoring application 136 may configure the at least one sensor device 140 (e.g., IoT devices) to monitor biometric data of the one or more patient 103 as specified by a care plan. For example, the monitoring application 136 could configure logic on a heart rate monitoring device worn by the patient to monitor the patient's heart rate. In turn, the monitoring application 136 can send the heart rate data to the workflow server 110 which determines if a heath event is triggered, and if so, executes a workflow to process the event as described above. In another embodiment, the heart rate monitoring device, upon detecting that a threshold condition has been satisfied, could generate and transmit a health event to the mobile device 135, which in turn transmits the health event to the workflow server 110 for processing. However, in other embodiments, some of the tasks performed by the workflow server 110 may be performed by the mobile device 135. That is, the workflow may include tasks performed by the mobile device 135 or the at least one sensor device 140 as well as tasks performed by the workflow server 110.

In one embodiment, the monitoring application 136 can include logic related to transferring data to the care provider environment 105 over the network 145. For example, in an embodiment, the monitoring application 136 can receive raw biometric data from the sensor devices 140 and can cull or de-duplicate the data before transmitting it to the care provider environment 105. This can result in reduced bandwidth usage for data transmission between the mobile device 135 and the care provider environment 105 over the network 145. As another example, the monitoring application 136 can prioritize data transmission to the care provider environment 105. In some circumstances the volume of data can be relatively large, and the mobile device 135 may have a slow or intermittent network connection. In an embodiment, the monitoring application can prioritize data transmission so that higher priority date received at the mobile device 135 after lower priority data, is transmitted first. As another example, the monitoring application 136 can pre-empt an ongoing data transmission with a higher priority data transmission. In an embodiment, data transmission from the mobile device 135 to the care provider environment 105 can take some time. Upon receiving critical or high priority data from the sensors 140, the mobile device 135 can interrupt an ongoing lower priority transmission to transmit the high priority data.

In one embodiment, the monitoring application 136 receives environmental data from the at least one sensor device 140. Generally, the environmental data informs the monitoring application 136 of environmental conditions in an area proximate to the at least one sensor device 140 and the user—e.g., a room in which the user is located. For example, the at least one sensor device 140 may detect an air quality or pollen count for the patient 103 having a respiratory ailment. In another example, the at least one sensor device 140 may track the user's movements or actions in an environment such as how many times at night the patient 103 goes to the bathroom or if the patient 103 is tossing and turning at night. This environmental data can then be used by the monitoring application 136 by itself, or in combination with the biometric data, to trigger health events which are processed by the workflow server 110.

In one embodiment, the monitoring application 136 may use an output device (e.g., a display or audio system) on the mobile device 135 to provide information to the patient 103. For example, when executing a workflow, one of the processing nodes 114 may ask the patient 103 if she is experiencing any symptoms. To obtain feedback from the patient 103, the monitoring application 136 may display a user interface (UI) on the mobile device 135 which permits the patient 103 to list symptoms. Moreover, the monitoring application 136 may also display general information related to a care plan or the at least one sensor device 140 such as the patient's heart rate or weight, status of the at least one sensor device 140, etc.

In one embodiment, the at least one sensor device 140 interacts with the monitoring application 136 and assists the patient 103 in reporting patient vitals and other information to the care provider environment 105. As shown, the at least one sensor device 140 may include a body sensor 141, a weighing scale 142, and a blood pressure cuff 143. Each of the at least one sensor device 140 may capture different vitals of the patient 103. For example, when applied to a body of patient 103, the body sensor 141 captures biometric data (e.g., heart rate, ECG data, etc.) in real-time. In addition, each of the at least one sensor device 140 may be configured to transmit body-related metrics electronically to the monitoring application 136 on the mobile device 135. In turn, the monitoring application 136 sends the captured metrics to the workflow server 110 which can be used to trigger health events which are processed using the processing nodes 114 and the queues 115.

In one embodiment, upon detecting an observation threshold has been reached, the at least one sensor device 140 performs an initial classification of the health event. In a particular embodiment, the mobile device 135 is configured to perform the initial classification of the health event. For example, the body sensor 141, upon detecting that ECG data collected from the patient 103 indicates an erratic heart behavior, could classify the health event as a cardiac event. This initial classification of the health event, along with the relevant ECG data (e.g., ECG data including a predetermined length of time before and after the event), could be transmitted to the mobile device 135 (e.g., over a Bluetooth® communications link) and the monitoring application 136 subsequently forwards the ECG data and the health event data on to the workflow server 110 over the network 145 (e.g., the Internet). Alternatively, instead of classifying the data, the monitoring application 136 may forward the raw, unprocessed sensor data to the workflow server 110 which uses one of the processing nodes 114 to identify and classify health events which are then processed in the workflow server 110.

Figure 2:
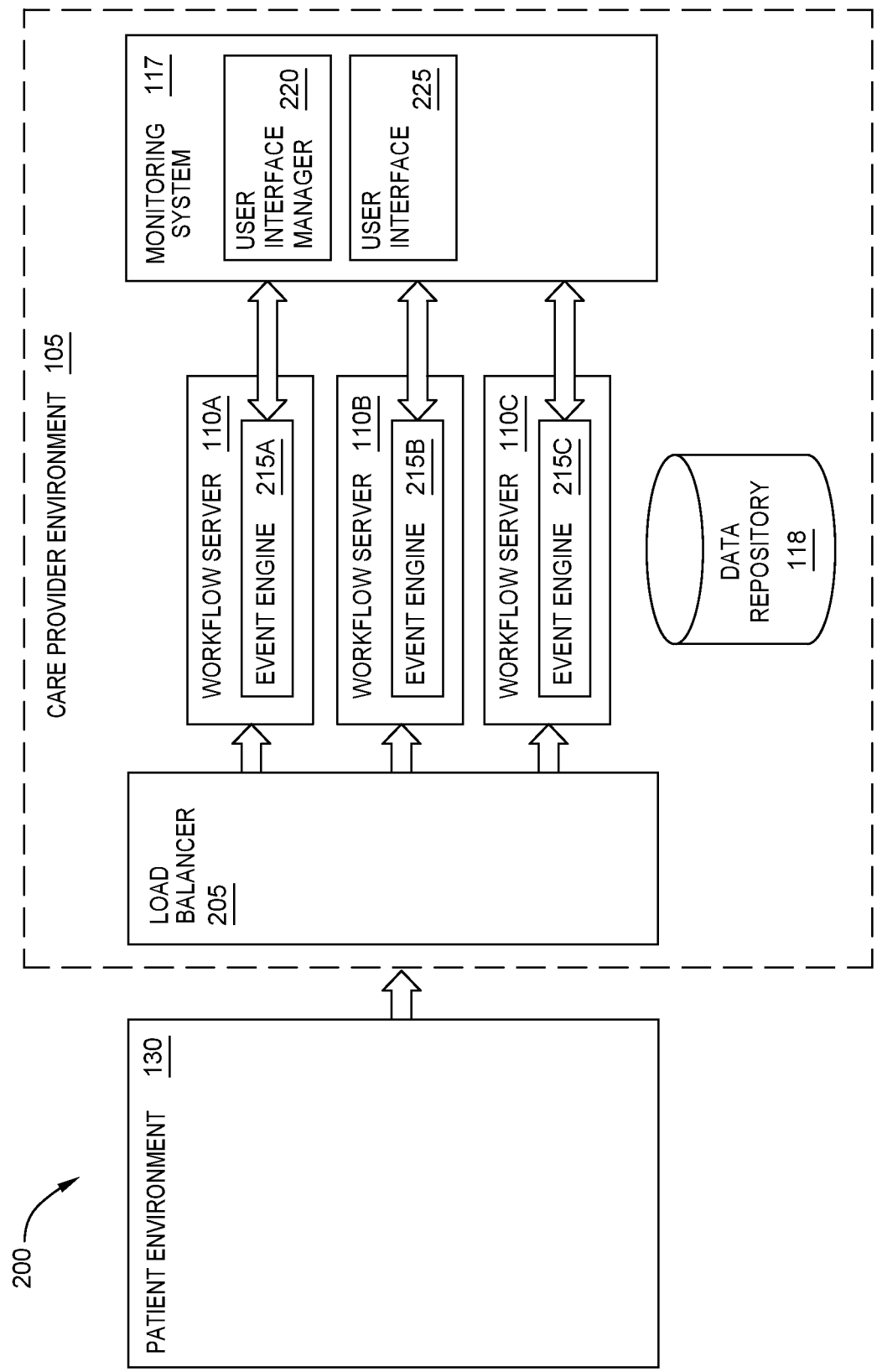
FIG. 2 illustrates a parallel processing computing environment, according to one embodiment.

FIG. 2 illustrates a parallel processing computing environment 200, according to one embodiment. As shown, the patient environment 130 transmits biometric data and/or health events to the care provider environment 105 which includes a load balancer 205. The workflow servers 110A-110C each include a respective one of the event engines 215A-215C. Although not shown, each of the event engines 215A-215C includes a plurality of interconnected processing nodes and queues that form a workflow for processing health events as discussed above. In one embodiment, the event engines 215A-215C each includes the same processing nodes and queues arranged in the same manner such that any one of the event engines 215A-215C can process the different health events generated by the at least one sensor device 140—i.e., any one of the event engines 215A-215C can process a cardiac event, respiratory event, maintenance event, etc. Based on current workload, the load balancer 205 transmits received data or heath events to one of the workflow servers 110A-110C for processing. For example, the load balancer 205 may assign the received health events in a round robin manner or by monitoring each respective central processing unit (CPU) or memory usage of the workflow servers 110A-110C.

Alternatively, the event engines 215A-215C may have different processing nodes and queues (or a different arrangement of the nodes and queues) such that the event engines 215A-215C are configured to process different event types. For example, the event engines 215A, 215B may have workflows that process cardiac events (and have the same processing nodes and queues), while the workflow in the event engine 215C processes respiratory events. The load balancer 205 may determine which of the event engines 215A-215C should receive the health event using the initial classification provided by the patient environment 130 or based on which of the at least one sensor device 140 measured the biometric data.

Regardless whether the event engines 215A-215C have the same arrangement or different arrangements, compute resources can easily be adjusted in response to varying workloads. For example, if additional sensor devices (e.g., sensor devices 140) are added to the patient environment 130, a system administrator can add additional ones of the workflow servers 110A-110C to process an increased number of received health events. The reverse is also true. If the number of health events decreases, the administrator may remove one or more of the workflow servers 110A-110C. For example, if the event engines 215A, 215B both process cardiac events but the number of cardiac events has decreased, the system administrator may remove one of the workflow servers 110A, 110B. As another example, a load balancer component could monitor the usage of computational resources by the workflow servers 110A-110C and could scale the number of servers up or down, based on the computational resource usage.

With continued reference to FIG. 2, the monitoring system 117 includes a user interface manager 220 (UI manager) and a user interface 225 (UI). As discussed above, the processing nodes 114 may require input from the care provider 101 (FIG. 1) in order to route the health events through the event engines 215A-215C. To do so, the event engines 215A-215C transmit requests to the UI manager 220 which generates the UI 225 which can be displayed to the care provider 101. For example, the UI manager 220 may generate the UI 225 that includes an electrocardiogram (ECG) chart corresponding to a cardiac event. Further, the UI 225 may include I/O features (e.g., buttons or pull down menus) that the care provider can use to provide input or instructions to one of the event engines 215A-215C. For example, the care provider may instruct the one of the event engines 215A-215C to store the cardiac event in the data repository 118, send the cardiac event to one of the queues 115 (FIG. 1) that is monitored by another care provider (e.g., to get a second opinion), or forward the cardiac event to the care provider 101 of the patient 103. Thus, the monitoring system 117 permits the workflow servers 110 to output information to the care provider 101 as well as receive instructions from the care provider 101.

The event engines 215A-215C may store data in and retrieve data from the data repository 118. For example, the event engines 215 may maintain a patient history by storing all the received health events (or selected health events) derived based on monitoring a patient's vitals in the repository 118. Further, the event engines 215A-215C may use the data stored in the data repository 118 to process the health events. For example, if one of the event engines 215A-215C receives biometric data indicating the current weight of the patient 103, then the one of the event engines 215A-215C can retrieve past weight measurements for the patient 103 from the data repository 118 and derive a trend graph detailing how the weight of the patient 103 has changed over time. For instance, the patient's current weight may not be enough to trigger a health event, but the patient's derived weight change over a period of time may trigger a health event. As discussed below, these derived trends may be used to generate a derived observation (or other event(s)).

In one embodiment, the event engines 215A-215C prioritize health events, which, in turn, determines how quickly the health events are processed by the workflows in the event engines 215A-215C or what processing nodes and queues are used to process the health events. As discussed above, the health events may be prioritized based on a severity of the health event, the type of the health event, a characteristic of the patient 103 whose biometric data generated the health event, and the like. Additionally, the health events could be prioritized based on additional criteria, such as an institutional policy, a care plan-level policy, a patient-level policy, another policy or some combination of the above.

Figure 3:
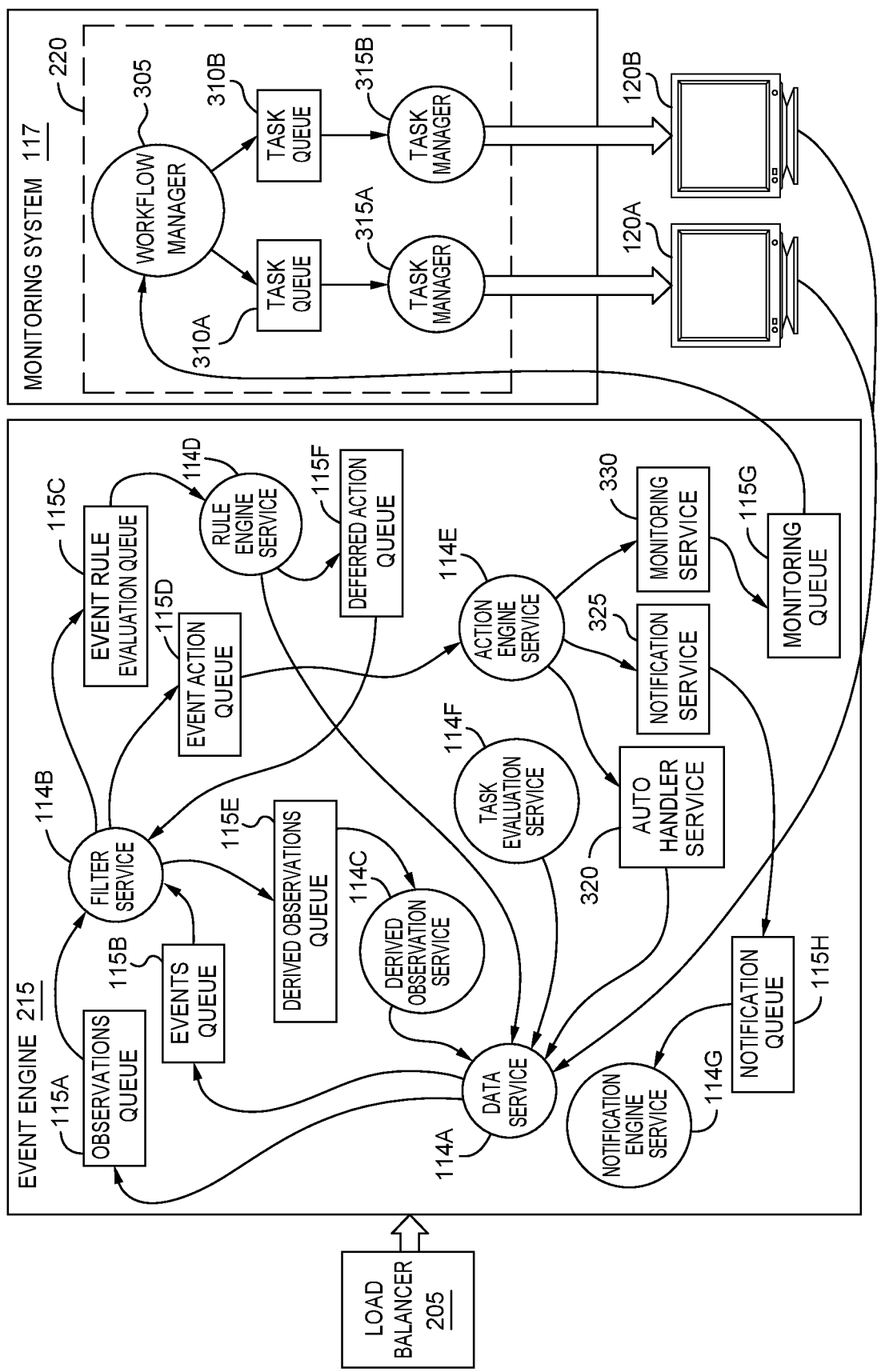
FIG. 3 illustrates an event engine for processing received health events, according to one embodiment.

FIG. 3 illustrates an event engine 215 that includes a workflow for processing health events, according to one embodiment. As described above, a health event or biometric data received from the sensors is forwarded from the load balancer 205 to the event engine 215. Specifically, a data service node 114A in the workflow receives the forwarded information from the load balancer 205. If the load balancer 205 forwards a health event, the data service node 114A classifies the health event based on type (e.g., a cardiac, respiratory, or maintenance event). In some cases, the health event was classified before being received by the data service node 114A. Nonetheless, the data service node 114A may review the data associated with the health event such as ECG data, breathing rate, blood pressure, etc. using more compute intensive techniques to determine whether the initial classification was correct. In another example, the data service node 114A may provide a more detailed classification of the health event than the initial classification. For example, the sensor device may have generated the health event because it detected an irregular heartbeat. However, the data service node 114A may evaluate the heartbeat and classify the health event as a specific cardiac health event—e.g., a ventricular trigeminy event or an atrioventricular block event. The data service node 114A may save the classification of the health event which is used by downstream nodes and queues to process the health event.

Instead of receiving a health event, the data service node 114A may receive raw data or observations from the patient environment. That is, the raw data or observations may not have been evaluated by a sensor device worn by the patient to determine if this data triggers a health event. For example, observation data from a sensor includes blood pressure measurements, weight measurements, ECG data, and the like. As discussed below, the event engine 215 evaluates these observations and can trigger health events which are then processed in the engine 215.

The data service node 114A forwards the observations to the observation queue 115A and the health events to the events queue 115B. A filter node 114B pulls the observations and health events stored in the queues 115A and 115B. This node 114B serves as a gatekeeper that determines where the health events and observations are routed for further processing. When evaluating observations, the filter node 114B may determine whether to ignore (i.e., drop) the observations or forward the observations to a derived observation queue 115E. For example, observations such as low battery signals, start signals indicating a sensor device has started collecting biometric data, or stop signals indicating a sensor device has stopped may be ignored by the filter service node 114B. In contrast, the node 114B may forward observations such as weight measurements, blood pressure measurements, ECG data, and the like to the derived observation queue 115E. In this manner, the filter service node 114B screens the incoming observations to determine whether they should be processed further such as checking for triggering health events.

Observations forwarded by the filter service node 114B are then processed by a derived observation service node 114C. This node 114C uses received observations in conjunction with previously received observations to create new observations or to generate a new health event. Stated differently, the derived observation service 114C may aggregate previously received observations with the currently received observations to compute statistics, trends, trigger health events, and the like. Although not shown, node 114C may be communicatively coupled to the data repository which stores past observations. For example, if the currently received observation is a weight measurement, the derived observation service node 114C may evaluate this measurement with previous weight measurements to determine a weight change for the patient over a defined period of time. This weight change may trigger a health event which is then forwarded to the data service node 114A for further processing. Even if a health event is not triggered, the derived observation service node 114C may store a derived observation (e.g., a weight change, average blood pressure, heart rate trends, etc.) in the data repository so that this data is available when further observations for the patient are received by the event engine 215 (or other event engines 215).

In one embodiment, health events may be processed by the derived observation service node 114C. For example, a sensor device may trigger a health event upon determining a patient's average blood pressure for a day exceeds a threshold. The filter service node 114B may forward this health event to the derived observation service node 114C which then may use past blood pressure measurements for that patient to derive a weekly or monthly average blood pressure for the patient, or a blood pressure trend graph. Based on this derived observation, the node 114C may generate a new health event or decide to drop the health event if the derived observation does not satisfy a corresponding condition.

Further, filter service node 114B also includes logic for determining whether received health events should be dropped, forwarded to an event action queue 115D, or forwarded to the event rule evaluation queue 115C. For example, a system administrator may determine that some health events are not relevant for certain patients. The logic in the filter service node 114B may identify and drop these health events to prevent them from propagating through the rest of the event engine 215. For instance, a patient may have a heart murmur that constantly results in a sensor device triggering a health event. Rather than continually processing these health events, a care provider can instruct the filter service node 114B to screen out (or suppress) these health events from the patient.

If a received health event has a corresponding action or actions, the filter service nodes 114B forwards the health event to the event action queue 115D. However, if the action for a health event has not yet been identified, the filter service node 114B forwards the health event to the event rule evaluation queue 115C. A rule engine service node 114D pulls the health events from the queue 115C and evaluates the health event using one or more rules. Example rules include determining whether daily weight change and average blood pressure exceed respective thresholds. Based on this evaluation, the node 114D may determine what action the event engine 215 should perform—e.g., suppress/ignore the event, auto handle the event, display the event to a care provider, or delay processing the event. Once the action is determined, the rule engine service node 114D generates and forwards a new health event that includes the corresponding action to the data service node 114A. Now that the corresponding action is known, once the new health event reaches the filter service node 114B, it forwards the event to the event action queue 115D rather than the event rule evaluation queue 115D.

The rule engine service node 114D may delay processing the health event by forwarding the event to a deferred action queue 115F. The node 114D may do so when there is not enough available computing power to perform the rule evaluation or if the rule evaluation has not yet completed. That is, if all of the rules have not yet been evaluated and further evaluation is required before triggering the event action, then the event may be placed in queue 115F. For example, the rule may trigger a cardiac event but the system must first check to determine if that event is suppressed for the patient before taking the corresponding action. As shown, the health events stored in the deferred action queue 115F are then retrieved by the filter service node 114B and can be reintroduced into the event rule valuation queue 115C at a later time—i.e., when all the rules have been evaluated.

Once a corresponding action for a health event is known and the health event is stored in the event action queue 115D, an action engine service node 114E routes the health event to the appropriate action service—i.e., auto handler service 315, notification service 320, or monitoring service 325. The auto handler service 315 may perform actions that do not require supervision or input by a care provider—e.g., stores the health event in the data repository. As another example, the auto handler service 320 may assign a priority or severity to the health event before the event is reintroduced into the workflow with the new priority. The auto handler service 320 may also generate a new health event when, for example, a health event shows a cardiac event but the data quality is low. In response, the service 320 may introduce a maintenance event for checking the sensor connection/electrodes.

The event engine 215 uses notification service 325 to send information to the patient, a care giver, car provider, or device regarding the health event. The notification service 325 may include different communication channels or techniques for communicating with the patient such as email, chat, SMS messages, etc. Although FIG. 3 illustrates only one notification queue 115H and notification engine service node 114G for handling requests, the event engine 215 may have different queues and notification nodes for the different communication techniques. For example, if a maintenance event is triggered when an electrode is unplugged from a sensor device, the notification service 325 may transmit an email to the patient's mobile device instructing the patient to plug in the electrode. Alternatively, if a respiratory event is triggered because of an elevated breathing rate, the notification service may send an SMS message to the patient asking her if she is currently performing a physical activity.

The monitoring service 330 communicatively couples the event engine 215 to the monitoring system 117. When input from a care provider regarding a health event is desired, the monitoring service 330 forwards the health event to a monitoring queue 115G. The UI manager 220 in the monitoring system 117 includes a workflow manager node 305 that pulls health events from the monitoring queue 115G and assigns them to either task queue 310A or 310B. The UI manager 220 also includes task manager nodes 315A and 315B which generate UIs for the health events. These UIs are then displayed to care providers via the computing devices 120A and 120B. Further, the task manager nodes 315 may place the biometric or maintenance data associated with the health events in the UIs. For example, a UI for a cardiac event may display an ECG graph and a baseline chart, while a UI for respiratory event displays a breathing rate and oxygen levels in the blood. In this manner, the UI manager 220 can generate a customized UI for the different health events.

The computing devices 120 may transmit information to the data service node 114A of the event engine 215 which can be used to generate new health events or update current health events. For example, the care provider may instruct the event engine 215 to take a certain action such as forwarding the health event to a different care provider to get a second opinion, reclassifying the health event, suppressing or ignoring the health event, notifying a health care provider, and the like. Based on the care provider's input, the event engine 215 again routes the health event through the nodes 114 and queues 115.

The event engine 215 also includes a task evaluation service node 114F. Unlike the other nodes and queues in event engine 215 which process or store observation data or health events received from the patient environment, the task evaluation service node 114F determines whether to trigger a health event based on a care protocol or care plan. In one embodiment, the node 114F triggers a health event when the patient does not follow the care protocol or plan.

For example, the care protocol may ask that the patient wear a sensor device for certain amount of time during the day or take weight measurements each day. By monitoring the observation and health events received by the event engine 215, the task evaluation service node 114F determines whether the patient has complied with the care protocol. If not, the task evaluation service node 114F triggers a health event with a corresponding action for the event engine 215 to perform such as sending a notification to the patient using notification service 325 or informing a care provider using the monitoring service 330.

Figure 4:
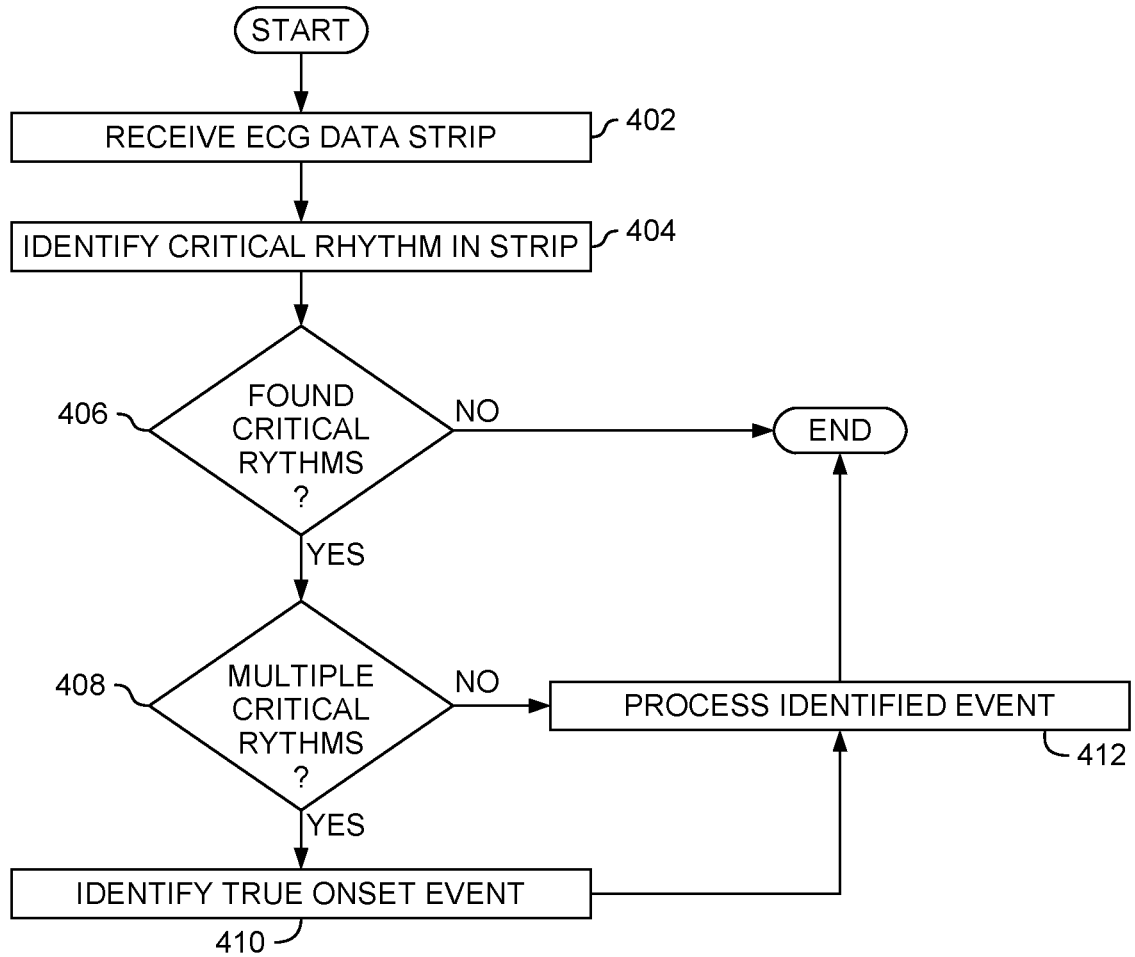
FIG. 4 is a flowchart for identifying true onset of a cardiac event, according to one embodiment.

FIG. 4 is a flowchart for identifying true onset of a cardiac event, according to one embodiment. At block 402, an event engine (e.g., the event engine 215 illustrated in FIGS. 2 and 3 or any other suitable module or component) receives an ECG data strip. In an embodiment, the techniques described in relation to FIG. 4 are performed by a server in the care provider environment (e.g., a workflow server 110 as illustrated in FIG. 1). There are several advantages to performing these techniques on a server, as opposed to a mobile device (e.g., the mobile device 135) or sensor device (e.g., one of the sensor devices 140). For example, a server typically has more computing resources than a mobile device or sensor. This allows for both faster, and more robust, analysis. Further, the techniques described in relation to FIG. 4 can be compute-resource intensive, causing a drain on battery life for a mobile device or sensor. Performing these techniques on a server, which typically has a dedicated power source, alleviates this concern. As another example, performing these techniques on a server can reduce the reliance on classification by sensor devices. Sensor devices typically have less processing power, and are sometimes less reliable, than a server. By identifying true onset events at the server, the system can reduce reliance on sensor devices to classify events, and can even make it so that sensor devices need not identify abnormal rhythms at all.

Alternatively, the techniques described in relation to FIG. 4 are performed by a mobile device (e.g., the mobile device 135). This also has several technical advantages. For example, the mobile device can receive the ECG data directly from the sensor devices, before sending the data to a server. This allows the mobile device to more quickly identify the true onset, allowing for rapid notifications or treatment. As another example, performing these techniques on a mobile device allows distribution of the processing among a large number of user devices, rather than on a centralized server. This can reduce server bandwidth and data processing requirements. Further, the care provider environment can be configured to divide performance of the techniques described in relation to FIG. 4 between a server and a mobile device (or sensor devices). For example, if a server in a care provider environment is overloaded or experiencing technical difficulties, a mobile device could perform these techniques to ensure the onset of critical events is identified in a timely manner. As another example, portions of these techniques could be performed on the server and portions performed on the mobile device (or sensor devices).

In an embodiment, the ECG data strip received by the event engine can be the result of a button press by a patient wearing a monitoring device. In an embodiment, the ECG data strip resulting from a button press is not further analyzed for a true onset and the techniques illustrated in FIG. 4 can be skipped. Alternatively, the ECG data strip resulting from a button press can also be analyzed using the techniques illustrated in FIG. 4.

Returning to FIG. 4, at block 404 the event engine identifies a critical rhythm in the strip of ECG data. In an embodiment, the event engine identifies the most critical rhythm at the beginning of the strip. In an embodiment, the event engine can be configured to ignore rhythms starting at the beginning of the strip. For example, a bit can be set in a table signifying whether classifications at the beginning of a strip should be ignored. If this bit is set, rhythms at the beginning of the strip will be ignored. If this bit is not set, rhythms at the beginning of the strip will be used. In an embodiment, this bit can be set uniformly for all rhythm types. Alternatively, this bit can vary between rhythm types (e.g., the bit can be set for some rhythm types and not for others). In an embodiment, this bit is pre-set. Alternatively, this bit can be configured based on user input.

In an embodiment, the event engine can be configured to retain first classifications that occur within a set time period of the beginning, or resumption, of monitoring for the patient. For example, the event engine can be configured to retain first classifications occurring within five minutes (or another suitable time period) of the beginning, or resumption, of monitoring.

At block 406, the event engine determines whether any critical rhythms have been found in the strip. If not, the flow ends. If so, the flow proceeds to block 408. At block 408, the event engine determines whether multiple critical rhythms have been found. If not, the flow proceeds to block 412. If so, the flow proceeds to block 410.

At block 410, the event engine identifies the true onset from among the multiple identified critical rhythms. In an embodiment, the event engine selects the rhythm with the highest priority. In an embodiment, the priority is a property of the type of event. For example, in an embodiment different categories of rhythms can be assigned different priorities. Table 1, below, illustrates an example list of rhythms that could be identified:

| Rhythm Description |
| --- |
| Ventricular Flutter |
| Ventricular Tachycardia |
| Pause |
| Sinus Bradycardia |
| Third Degree (Complete) Heart Block |
| Atrial/Supraventricular Tachycardia |
| Slow Ventricular Tachycardia |
| Atrial Fibrillation/Flutter RVR |
| Second Degree Heart Block Type II |
| Ventricular Run |
| Slow Ventricular Run |
| Idioventricular Rhythm |
| Accelerated Idioventricular Rhythm |
| Atrial Fibrillation/Flutter CVR |
| Sinus Bradycardia + IVCD |
| Sinus Tachycardia + ICVD |
| Second Degree Heart Block Type I |
| Sinus Tachycardia |
| First Degree Heart Block + Sinus Bradycardia |
| Atrial Fibrillation/Flutter SVR |
| First Degree Heart Block + Sinus Tachycardia |
| Junctional Tachycardia |

In an embodiment, each of these rhythms can be assigned a different priority. Alternatively, groups of rhythms can be assigned a priority. As another alternative, some, but not all, rhythms can be assigned a priority. As discussed above, in an embodiment, the event engine selects the rhythm with the highest priority. If multiple events with the same highest priority are found, the event engine selects the event with the greatest (duration*confidence). In an embodiment, the event engine (or another suitable component) can analyze the strip to determine a duration of the event and a confidence level in the classification of the event. The event engine can then use these values when selecting a rhythm.

Further, in an embodiment, various threshold properties can be used when classifying a rhythm from the ECG strip data (e.g., identifying one of the rhythms illustrated in FIG. 1). For example, some, or all, of the rhythms can include a minimum heartrate threshold, a maximum heartrate threshold, and a minimum heartbeats threshold. In this example, the event engine classifies a portion of the ECG data as representing a given rhythm only when each of these thresholds is met: the identified data must include a heartrate greater than the minimum heartrate threshold and less than the maximum heartrate threshold, and must include more than the minimum heartbeat threshold. Further, in an embodiment, the event engine uses a minimum confidence threshold. If the confidence level for the identified rhythm falls below the minimum confidence threshold, the event engine will not classify the data with that rhythm type. These are merely examples of suitable threshold categories and values. In an embodiment some, but not all, of these threshold values are used. Further, additional suitable threshold values can be used. Or, alternatively, no thresholds can be used.

In an embodiment the event engine can further identify a time period around the identified onset event (e.g., 60 seconds). The event engine can split both the ECG data and the findings to mirror the identified time period. This is discussed in more detail with regard to FIG. 6. The flow then proceeds to block 412.

At block 412, the event engine processes the identified event. This is discussed in more detail with regard to FIG. 5.

Figure 5:
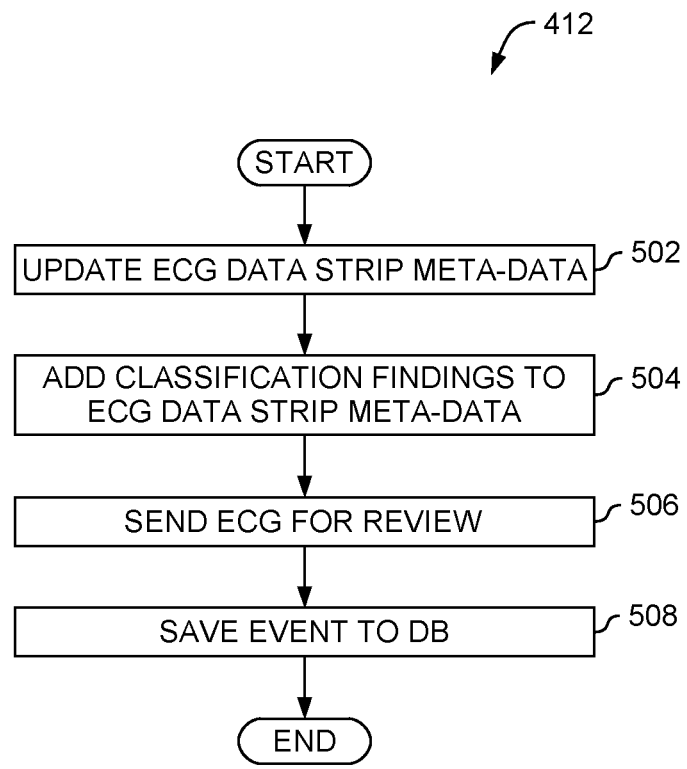
FIG. 5 is a flowchart for processing an identified event, according to one embodiment.

FIG. 5 is a flowchart for processing an identified event, according to one embodiment. In an embodiment, FIG. 5 corresponds with block 412 illustrated in FIG. 4. At block 502, an event engine (e.g., the event engine 215 illustrated in FIGS. 2 and 3 or any other suitable module or component) updates the ECG data strip meta-data. In an embodiment, the event engine adds or modifies meta-data information or properties related to the ECG data strip. For example, the event engine can add or modify time and duration data for the ECG data strip, based on the identified onset and the selected slice of ECG data. Further, the event engine can add or modify the trigger-type. In an embodiment, the trigger-type associated with an ECG data strip represents the highest priority, or most important, event. This trigger-type can be used to determine processing priority (e.g., as discussed above with respect to FIG. 3) for the ECG data strip and other values.

In an embodiment, an initial trigger-type for an ECG data strip uploaded for analysis is a relatively low acuity event (e.g., a broadly identified irregularity). This trigger type can be saved in meta-data associated with the ECG data strip. The event engine analyzes the ECG data and identifies a higher acuity event. The event engine can then update the trigger-type value, replacing the broadly defined initial event with the more specific (and potentially higher acuity (e.g., higher priority)) event. Additional meta-data properties can also be updated, including record-date, average heart-rate, duration in milliseconds, pre- and post-time, sample rate, and any other suitable properties. In an embodiment, all, none, or some of these properties can be added or modified at block 502.

At block 504, the event engine adds classification findings to the ECG data strip meta-data. For example, the event engine can add the classification for the onset event to the ECG data. Further, the event engine can add classification data for any other events identified in the ECG data (e.g., events other than the onset event). In an embodiment, an interested party reviewing the ECG data strip may be most interested in the onset event, but may wish to view the other identified events as well. Further, a reporting or monitoring tool may use this event data. At block 506, the event engine sends the ECG data for review (e.g., to a physician or to a monitoring service). At block 508 the event engine saves the identified onset event to an electronic database. Any suitable electronic database can be used, including a relational database or any other suitable data storage location. In an embodiment, the onset event can be saved with a duration of 0 milliseconds, or with any other suitable duration.

In an embodiment, performing the techniques illustrated in FIGS. 4 and 5 will result in several outcomes. As one example, a header property identifying when an event occurred will be updated to reflect the time of the true onset of the event. As another example, the event type will accurately reflect the true onset event (rather than, e.g., a later event stemming from the true onset event). As another example, additional properties will be updated, including pre- and post-time, average heart-rate, and duration properties.

Further, as another example, if the ECG data strip did not relate to a trigger (e.g., a button press), an ECG slice with an interval around the true onset event will be generated (e.g., a 60 second interval). Both the ECG data and classification findings can be sliced around the onset. As another example, unreliable events can be filtered in order to eliminate on-going rhythms where the onset occurred prior to the current strip. For example, as discussed above, events occurring at the beginning of a strip can be filtered out in some circumstances. As another example, a second event in a strip can be filtered out if toggling between rapid ventricular rate (RVR)/controlled ventricular rate (CVR) or slow ventricular rate (SVR)/CVR, the first classification was skipped, and a second atrial fibrillation event immediately follows the first event. As another example, artifacts that split up rhythm classifications can be identified and removed by identifying the initial onset.

Figure 6:
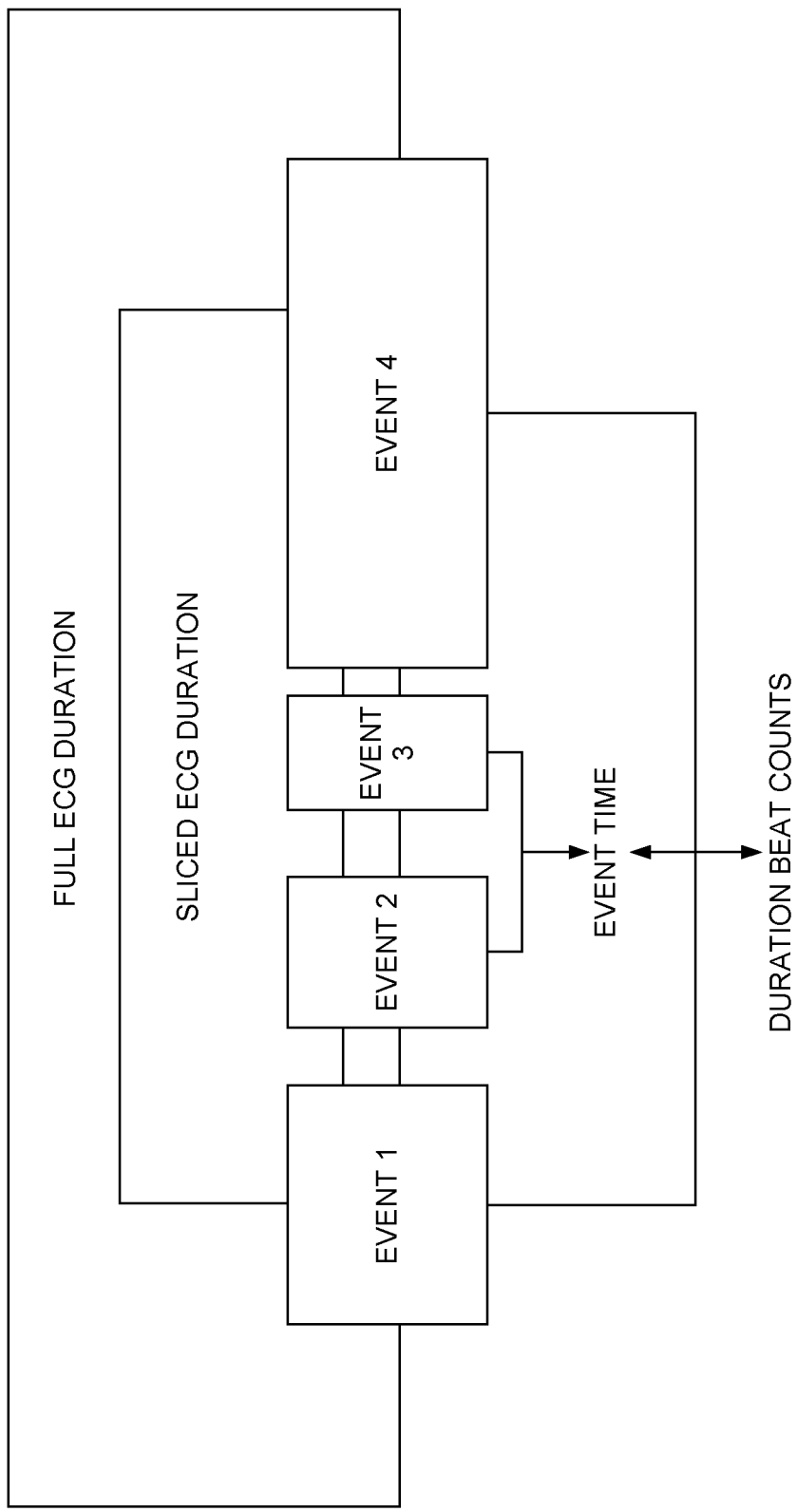
FIG. 6 illustrates slicing an ECG data strip, according to one embodiment.

FIG. 6 illustrates slicing an ECG data strip, according to one embodiment. In an embodiment, an ECG data strip includes a relatively long collection of data (e.g., 5 minutes, 30 minutes, 60 minutes, or longer). In an embodiment, instead of providing all of this data for display to a care provider or other interested party, the event engine can generate a slice of data surrounding the onset of the condition and present that data. As illustrated in FIG. 6, for example, the event engine identifies four events in a full ECG data strip: Event 1, Event 2, Event 3, and Event 4. The event engine determines that Event 3 marks an onset. The event engine then identifies ECG data covering a specified time before and after the onset event (e.g., 1 minute before and after Event 3). The event engine generates the Sliced ECG Duration from the Full ECG Duration, and provides the ECG data falling within the sliced ECG duration to the next level of the system (e.g., the reporting system, monitoring system, care provider, or other interested party).

In an embodiment, the user interface provided to care providers can be modified to account for identification of the true onset. For example, the true onset can be identified in the user interface (or reports) using a special label or symbol. Further, the true onset can be presented using a new display format differentiating the true onset from other events. The user interface (or reports) can be modified to describe (or emphasize) the true onset. For example, lines or grids in the user interface (or reports) can be aligned based on the true onset. Further, overlay or hover text or symbols can be used.

Figure 7:
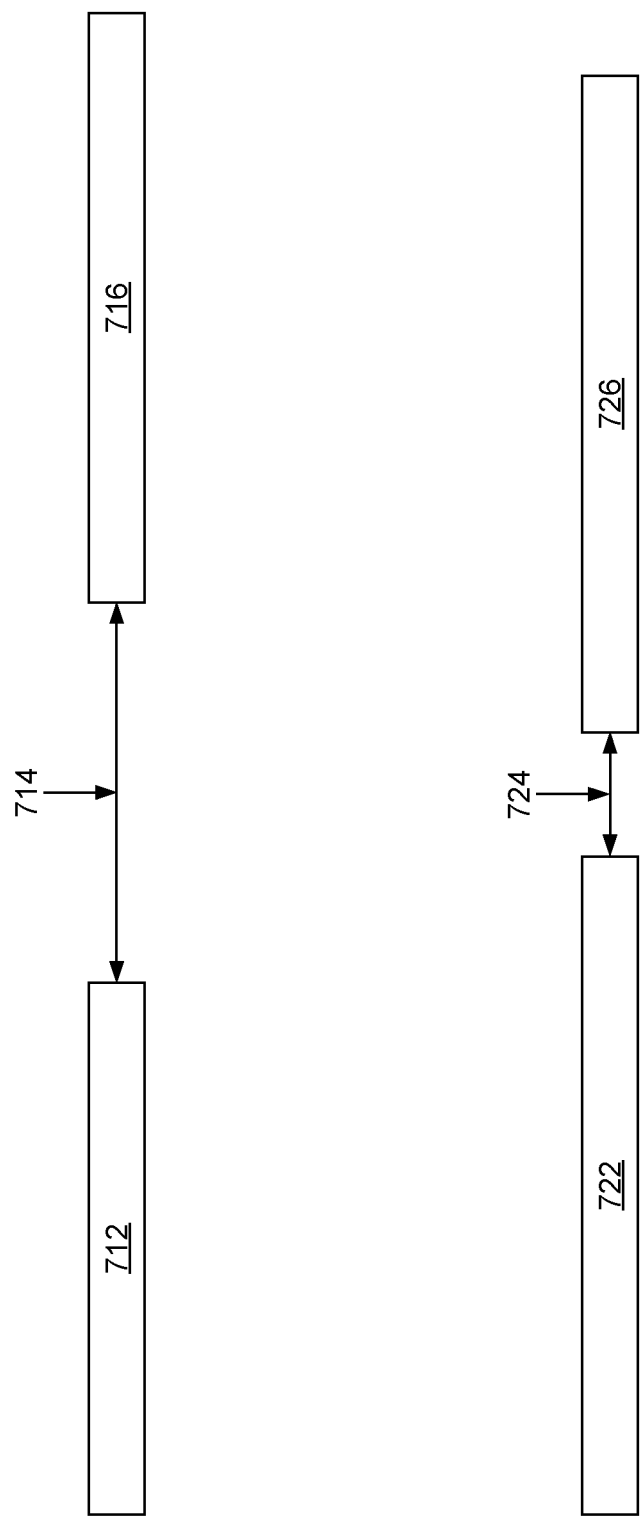
FIG. 7 illustrates bridging events from an ECG data strip, according to one embodiment.

FIG. 7 illustrates bridging events from an ECG data strip, according to one embodiment. In an embodiment, an event handler might classify a slice of ECG data to include two instances of the same rhythm type, with a gap between the rhythms. For example, as illustrated in FIG. 7, rhythms 712 and 716 could be like rhythms (e.g., both could be tachycardia rhythms) with a time gap 714 between them.

In some circumstances, the event handler can generate bridged ECG data by bridging the like rhythms 712 and 714, eliminating the time gap 714.

In particular, in an embodiment, an open area where there is no other burden event (afib, brady, tachy) could be eligible to be joined. For example, particular markers (afib, brady, tachy), artifacts, and normal sinus rhythm (NSR) could be evaluated when bridging over gap. In this example, other classification markers (in addition to any artifacts) could be bridged.

Many different criteria can be used when deciding whether to bridge a gap. In one embodiment, the following technique could be used: If (GapDuration<min(B, max (A, C))), then bridge the gap. In this equation, GapDuration is the time duration of the gap (e.g., in seconds). The variable A represents a floor value that acts as a minimum gap duration below which a gap will always be a candidate for bridging (e.g., a very short duration). The variable B represents a maximum interval, by rhythm marker type, over which two like rhythms can be bridged. The variable C represents a confidence interval factor. For example, C can represent a confidence interval factor applied to the sum of the duration of both events surrounding the gap: C=(factorC*(event1duration+event2duration)).

In an embodiment, additional factors can be used to exclude gaps from bridging. For example, a gap should not be bridged if it includes missing ECG data (e.g. ECG data that is missing because the heart monitoring device was disconnected.) As another example, some rhythm types can be marked as excluded from bridging. As another example, users can mark some rhythm types or gap types as excluded from bridging. As another example, events occurring over midnight in the patient's time zone may not be bridged. Returning to FIG. 7, in an embodiment, the events 712 and 716 would not be bridged because the gap 714 is too long, while the events 722 and 726 would be bridged because the gap 724 is sufficiently short.

FIG. 8 further illustrates bridging events from an ECG data strip, according to one embodiment. In an embodiment, as illustrated in FIG. 7, like rhythm events separated by a blank reading may be bridged. Further, as illustrated in FIG. 8, like rhythm events separated by particular types of intervening events may also be bridged. For example, the events 812 and 816 could be tachycardia events separated by an afib event. Because tachycardia and afib events can overlap, the events 812 and 816 should be bridged, and an additional afib event representing the event 814 should be created and inserted. As another example, the events 822 and 826 could be separated by an artifact 824. The events 822 and 826 could be bridged, and the artifact 824 could be removed.

Further, bridging can be controlled based on user input. For example, a user could create a bridged event when reviewing consecutive events with a gap. As another example, as discussed above, a user could exclude a rhythm event from bridging. As another example, a user could re-classify an event, causing bridging to occur between the re-classified event and a neighboring event (e.g., the re-classified event is now the same type as a neighboring event).

In addition to bridging neighboring events, as discussed above, in some circumstances an event handler can split events. For example, a user might create a merged event over a period of time. The event handler might determine that the user-created event actually includes two events of different types. If the event handler is sufficiently confident in its determination (and subject to user settings and any other suitable determinations or criteria), the event handler can split the event.

In the preceding, reference is made to embodiments presented in this disclosure. However, the scope of the present disclosure is not limited to specific described embodiments. Instead, any combination of the described features and elements, whether related to different embodiments or not, is contemplated to implement and practice contemplated embodiments. Furthermore, although embodiments disclosed herein may achieve advantages over other possible solutions or over the prior art, whether or not a particular advantage is achieved by a given embodiment is not limiting of the scope of the present disclosure. Thus, the preceding aspects, features, embodiments and advantages are merely illustrative and are not considered elements or limitations of the appended claims except where explicitly recited in a claim(s).

As will be appreciated by one skilled in the art, the embodiments disclosed herein may be embodied as a system, method or computer program product. Accordingly, aspects may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects may take the form of a computer program product embodied in one or more computer readable medium(s) having computer readable program code embodied thereon.

Any combination of one or more computer readable medium(s) may be utilized. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium is any tangible medium that can contain, or store a program for use by or in connection with an instruction execution system, apparatus or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present disclosure may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present disclosure are described below with reference to flowchart illustrations and/or block diagrams of methods, apparatus (systems) and computer program products according to embodiments presented in this disclosure. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams in the Figures illustrate the architecture, functionality and operation of possible implementations of systems, methods and computer program products according to various embodiments. In this regard, each block in the flowchart or block diagrams may represent a module, segment or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

We claim:

1. A method carried out by a server, the method comprising:
    determining, using the server, that a first strip of electrocardiogram (ECG) data includes cardiac events each comprising one or more critical rhythms;
    calculating, by the server, a confidence level associated with the critical rhythms;
    determining, by the server, that the confidence level is above a minimum confidence threshold;
    associating, by the server, the cardiac events with an initial classification in response to the determining that the confidence level is above a minimum confidence threshold;
    identifying, by the server, which one of the cardiac events is as an onset event;
    identifying which of the cardiac events is a later event stemming from the onset event;
    slicing the first strip of ECG data into a shorter strip to exclude the later event;
    modifying, at the server, the initial classification of the cardiac event identified as the onset event; and
    modifying the ECG data, using the server by:
        generating meta-data for the ECG data based on the onset event, and
        modifying the ECG data to include the generated meta-data.

2. The method of claim 1, wherein the identifying which one of the cardiac events is the onset event is based on a priority of at least one of the critical rhythms.

3. The method of claim 2, wherein the identifying which one of the cardiac events is the onset event is further based on a duration of the at least one of the critical rhythms and the confidence level.

4. The method of claim 1, wherein the meta-data comprises data relating to at least one of: trigger-type, heart-rate, or sample rate.

5. The method of claim 1, further comprising:
    generating a slice of the first strip of ECG data, the slice comprising data for a first pre-determined interval prior to the onset event and data for a second pre-determined interval subsequent to the onset event;
    filtering out the later event; and
    transmitting the slice of ECG data to a patient care provider.

6. The method of claim 1, wherein the onset event includes a first tachycardia event occurring at a first time, the method further comprising:
    identifying a second tachycardia event in the ECG data occurring at a second time, after a conclusion of the first tachycardia event; and
    generating bridged ECG data comprising the first tachycardia event and the second tachycardia event.

7. The method of claim 6, further comprising:
    identifying a time gap between the conclusion of the first tachycardia event and a beginning of the second tachycardia event;
    determining, based on the time gap, that the first tachycardia event and the second tachycardia event should be bridged; and
    in response, generating the bridged ECG data, wherein the bridged ECG data does not include the time gap.

8. The method of claim 6, wherein the generating the bridged ECG data comprises inserting a third cardiac event between the first tachycardia event and the tachycardia cardiac event, wherein the third cardiac event is an atrial fibrillation event.

9. A non-transitory computer-readable medium containing computer program code that, when executed on a computer processor, performs an operation comprising:
- determining that a first strip of electrocardiogram (ECG) data includes cardiac events each comprising one or more critical rhythms;
- calculating a confidence level associated with the critical rhythms;
- determining that the confidence level is above a minimum confidence threshold;
- associating the cardiac events with an initial classification in response to the determining that the confidence level is above a minimum confidence threshold;
- identifying which one of the cardiac events is an onset event;
- identifying which of the cardiac events is a later event stemming from the onset event;
- modifying the initial classification of the cardiac event identified as the onset event;
- modifying the ECG data based on the identified onset event, comprising:
  - generating meta-data for the ECG data based on the onset event; and
  - modifying the ECG data to include the generated meta-data;
- slicing the first strip of ECG data into a shorter strip to exclude the later event.

10. The non-transitory computer-readable medium of claim 9, wherein the identifying which one of the cardiac events is the onset event is based on a priority of at least one of the critical rhythms, a duration of at least one of the critical rhythms, and the confidence level.

11. The non-transitory computer-readable medium of claim 9, the operation further comprising:
- identifying a time gap between the conclusion of the onset event and a beginning of another cardiac event occurring between the onset event and the later event;
- determining, based on the time gap, that the onset event and the another cardiac event should be bridged; and
- in response, generating bridged ECG data comprising the onset event and the another cardiac event, wherein the bridged ECG data does not include the time gap.

12. A system comprising:
- a processor; and
- a memory storing a program, which, when executed on the processor, performs an operation, the operation comprising:
  - determining that a first strip of electrocardiogram (ECG) includes cardiac events each comprising one or more critical rhythms;
  - calculating a confidence level associated with the critical rhythms;
  - determining that the confidence level is above a minimum confidence threshold;
  - associating the cardiac events with an initial classification in response to the determining that the confidence level is above a minimum confidence threshold;
  - identifying which one of the cardiac events is an onset event;
  - identifying which of cardiac events is a later event stemming from the onset event;
  - modifying the initial classification of the cardiac event identified as the onset event;
  - slicing the first strip of ECG data into a shorter strip to exclude the later event; and
  - modifying the ECG data based on the onset event, comprising:
    - generating meta-data for the ECG data based on the onset event; and
    - modifying the ECG data to include the generated meta-data.

13. The system of claim 12, wherein the identifying which one of the cardiac events is the onset event is based on a priority of at least one of the critical rhythms, a duration of at least one of the critical rhythms, and the confidence level.

14. The system of claim 12, wherein the shorter strip comprises data for a first pre-determined interval prior to the onset event and data for a second pre-determined interval subsequent to the onset event.

15. The system of claim 12, wherein the processor and the memory are parts of a server.

* * * * *